United States Patent
Christoph et al.

(10) Patent No.: US 6,908,944 B2
(45) Date of Patent: Jun. 21, 2005

(54) USE OF 6-DIMETHYLAMINOMETHYL-1-PHENYL-CYCLOHEXANE COMPOUNDS FOR TREATMENT OF URINARY INCONTINENCE

(75) Inventors: Thomas Christoph, Aachen (DE); Elmar Friderichs, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/448,442

(22) Filed: May 30, 2003

(65) Prior Publication Data

US 2004/0043968 A1 Mar. 4, 2004

Related U.S. Application Data

(63) Continuation of application No. PCT/EP01/13909, filed on Nov. 28, 2001.

(30) Foreign Application Priority Data

Nov. 30, 2000 (DE) .......................................... 100 59 411

(51) Int. Cl.⁷ ........................ A61K 31/44; A61K 31/34; A61K 31/135
(52) U.S. Cl. ........................ 514/469; 514/351; 514/647
(58) Field of Search ................................ 514/647, 469, 514/351

(56) References Cited

U.S. PATENT DOCUMENTS 5,733,936 A   3/1998   Buschmann et al.

FOREIGN PATENT DOCUMENTS

DE   19525137   1/1997
EP   1005861    6/2000

*Primary Examiner*—Raymond J. Henley, III
(74) *Attorney, Agent, or Firm*—Crowell & Moring LLP

(57) ABSTRACT

A pharmaceutical composition comprising a pharmaceutically acceptable excipient and a compound of formula I:

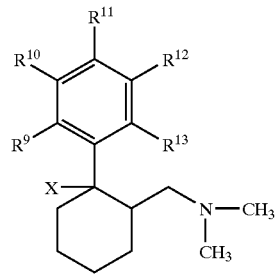

It has been surprisingly discovered that the pharmaceutical composition of the present invention is effective for the treatment of increased urge to urinate or urinary incontinence. Also disclosed are methods of treatment using the pharmaceutical compositions.

35 Claims, No Drawings

USE OF 6-DIMETHYLAMINOMETHYL-1-PHENYL-CYCLOHEXANE COMPOUNDS FOR TREATMENT OF URINARY INCONTINENCE

CROSS REFERENCE TO RELATED APPLICATIONS

The present application is a continuation of International Patent Application No. PCT/EPO1/13909, filed Nov. 28, 2001, designating the United States of America and published in German as WO 02/43712 A2, the entire disclosure of which is incorporated herein by reference. Priority is claimed based on Federal Republic of Germany Patent Application No. 100 59 411.5, filed Nov. 30, 2000.

FIELD OF THE INVENTION

The invention relates to the use of 6-dimethylaminomethyl-1-phenyl-cyclohexane compounds for treatment of an increased urge to urinate or urinary incontinence.

BACKGROUND OF THE INVENTION

Urinary incontinence is the involuntary discharge of urine. This occurs in an uncontrolled manner when the pressure within the urinary bladder exceeds the pressure needed to close the ureter. Causes can be on the one hand an increased internal pressure in the bladder (e.g. due to detrusor instability) with the consequence of urgency incontinence and on the other hand a reduced sphincter pressure (e.g. following giving birth or surgical interventions) with the consequence of stress incontinence. The detrusor is the coarsely bundled multilayered bladder wall musculature, contraction of which leads to the discharge of urine. The sphincter is the closing muscle of the urethra. Mixed forms of these types of incontinence and so-called overflow incontinence (e.g. in cases of benign prostate hyperplasia) or reflex incontinence (e.g. following damage to the spinal cord) also occur. Further details in this respect are found in Chutka, D. S. and Takahashi, P.Y., 1998, drugs 560: 587–595.

The urge to urinate is caused by increased bladder muscle tension as the bladder capacity is approached (or exceeded), prompting the discharge of urine (miction). The increased tension acts as a stimulus to miction. An increased urge to urinate is understood in the context of the present invention as meaning the occurrence of a premature or increased and sometimes even painful urge to urinate up to the so-called strangury. This consequently leads to significantly more frequent miction. Causes can be, inter alia, inflammations of the urinary bladder and neurogenic bladder disorders, and also bladder tuberculosis. However, all causes have not yet been clarified.

An increased urge to urinate and urinary incontinence are perceived as extremely unpleasant and there is a clear need among persons afflicted by these conditions to achieve an improvement which is as long-term as possible.

An increased urge to urinate and in particular urinary incontinence are conventionally treated with substances involved in the reflexes of the lower urinary tract (Wein, A. J., 1998, Urology 51 (suppl. 21): 43–47). These are usually medicaments which have an inhibiting action on the detrusor muscle, which is responsible for the internal pressure in the bladder. These medicaments are e.g. parasympatholytics, such as oxybutynin, propiverine or tolterodine, tricyclic antidepressants, such as imipramine, or muscle relaxants, such as flavoxate. Other medicaments, which in particular increase the resistance of the urethra or of the neck of the bladder, show affinities for α-adrenoreceptors, such as ephedrine, for β-adrenoreceptors, such as clenbutarol, or are hormones, such as estradiol. Certain opioids, e.g., diarylmethylpiperazines and piperidines, are also described for this indication in WO 93/15062. For tramadol, a positive effect on bladder function has been demonstrated in a rat model of rhythmic bladder contractions (Nippon-Shinyaku, WO 98/46216).

Generally, treatment of increased urge to urinate or urinary incontinence requires very long-term uses of medicaments. This is in contrast to many other situations where analgesics are employed. Urinary incontinence patients are faced with a condition which is very unpleasant but not intolerable. Therefore treatment of this condition must ensure—even more so than with other use of analgesics—that side effects of the analgesics are avoided, if the patient is not to be forced to exchange one evil for another. In addition, analgesic actions of the pharmaceutical compositions are largely undesirable and should be avoided during long-term treatment of urinary incontinence.

DESCRIPTION OF THE INVENTION

The object of the present invention is therefore to discover substances which are helpful for treatment of an increased urge to urinate or urinary incontinence and at active doses preferably simultaneously show fewer or decreased side effects and/or analgesic actions than known from the prior art.

Surprisingly, it has now been found that compounds according to general formula I have an outstanding action on bladder function and accordingly are particularly suitable for the treatment of increased urge to urinate or urinary incontinence.

The invention accordingly provides a pharmaceutical composition comprising a 6-dimethylaminomethyl-1-phenyl-cyclohexane compound according to general formula I

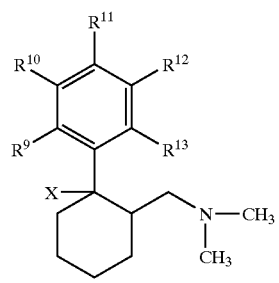

I wherein

X is OH, F, Cl, H or OC(O)R$^7$, where R$^7$ is C$_{1-3}$-alkyl, branched or unbranched, saturated or unsaturated, unsubstituted or mono- or polysubstituted, and R$^9$ to R$^{13}$ in each case independently of one another are H, F, Cl, Br, I, CH$_2$F, CHF$_2$, CF$_3$, OH, SH, OR$^{14}$, OCF$_3$, SR$^{14}$, NR$^{17}$R$^{18}$, SOCH$_3$, SOCF$_3$, SO$_2$CH$_3$, SO$_2$CF$_3$, CN, COOR$^{14}$, NO$_2$, CONR$^{17}$R$^{18}$; C$_{1-6}$-alkyl, branched or unbranched, saturated or unsaturated, unsubstituted or mono- or polysubstituted; or phenyl, unsubstituted or mono- or polysubstituted;

where R$^{14}$ is C$_{1-6}$-alkyl; pyridyl, thienyl, thiazolyl, phenyl, benzyl or phenethyl, in each case unsubstituted or mono- or polysubstituted; $PO(O-C_{1-4}\text{-alkyl})_2$, $CO(OC_{1-5}\text{-alkyl})$, $CONH-C_6H_4-(C_{1-3}\text{-alkyl})$, $CO(C_{1-5}\text{-alkyl})$, $CO-CHR^{17}-NHR^{18}$, or $CO-C_6H_4-R^{15}$, where $R^{15}$ is ortho-$OCOC_{1-3}$-alkyl or meta- or para-$CH_2N(R^{16})_2$, where $R^{16}$ is $C_{1-4}$-alkyl or 4-morpholino, wherein the alkyl groups in the radicals $R^{14}$, $R^{15}$ and $R^{16}$ to be branched or unbranched, saturated or unsaturated, unsubstituted or mono- or polysubstituted;

where $R^{17}$ and $R^{18}$ in each case independently of one another are H; $C_{1-6}$-alkyl, branched or unbranched, saturated or unsaturated, unsubstituted or mono- or polysubstituted; or phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, $OCH=CH$, $CH=CHO$, $CH=C(CH3)O$, $OC(CH3)=CH$, $(CH_2)_4$ or $OCH=CHO$ ring, in the form of a racemate; an enantiomer, a diastereomer, in particular a mixture of enantiomers or diastereomers, a mixture of diastereomers, a base, or a salt of a physiologically acceptable acid, and a pharmaceutically acceptable excipient.

The pharmaceutical composition of the present invention is suitable for the treatment of an increased urge to urinate or urinary incontinence.

Surprisingly, it has been found that compounds of formula I significantly improve a physiological parameter which is of importance in cases of an increased urge to urinate or urinary incontinence. Specifically, the compounds reduce the inter-contraction interval, or reduces the rhythmic bladder contractions. This reduction can mean a significant alleviation of the symptoms of the patients. Corresponding compounds and their preparation are known from DE 195 25 137 A1, the content of which is incorporated herein in its entirety.

The above activity of compounds of formula I significantly exceeds that of tramadol. Tramadol is known and is excluded from the present invention. In other words, the use of a compound according to formula I in which X corresponds to OH, $R^9$, $R^{11}$ and $R^{13}$ correspond to H and one of $R^{10}$ or $R^{12}$ corresponds to H, and the other corresponds to $OCH_3$ is excluded.

In the context of this invention, alkyl radicals are understood as meaning saturated or unsaturated, branched or unbranched hydrocarbons, which can also be at least monosubstituted. Preferred alkyl radicals are methyl, ethyl, vinyl (ethenyl), propyl, allyl (2-propenyl), 1-propinyl, methylethyl, n-butyl, sec-butyl, tert-butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, $CHF_2$, $CF_3$ or $CH_2OH$.

Cycloalkyl radicals in the context of this invention are furthermore understood as meaning saturated cyclic hydrocarbons, which can also be at least monosubstituted. Preferred cycloalkyl radicals are cyclopropyl, cyclobutyl, cyclopentyl, cyclohexyl or cycloheptyl.

In connection with alkyl and cycloalkyl, the term substituted is understood as meaning substitution of a hydrogen radical for F, Cl, Br, I, $NH_2$, SH or OH, "polysubstituted" to be understood as meaning that the substitution takes place on different or on the same atoms two or more times with the same or different substituents, for example three times on the same C atom as in the case of $CF_3$ or in various places as in the case of $-CH(OH)-CH=CH-CHCl_2$.

In connection with phenyl, benzyl or phenethyl, substituted is understood here as meaning preferably substitution of H with F, Cl, Br, I $CH_2F$, $CHF_2$, $CF_3$, OH, SH, $OR^{19}$, $OCF_3$, $SR^{19}$, $NH2$, $CONH_2$, $SOCH_3$, $SOCF_3$, $SO_2CH_3$, $SO_2CF_3$, CN, $COOR^{19}$, $NO_2$; $C_{1-6}$-alky, branched or unbranched, saturated or unsaturated, unsubstituted or mono- or polysubstituted; or phenyl, unsubstituted;

where $R^{19}$ is $C_{1-6}$-alkyl, branched or unbranched, saturated or unsaturated, unsubstituted or mono- or polysubstituted; or $C_{3-7}$-cycloalkyl.

Suitable salts in the context of this invention are salts of a particular active compound with inorganic or organic acids, or a sugar substitute, such as saccharin, cyclamate or acesulfam. However, the hydrochloride is particularly preferred.

The use of compounds according to formula I wherein X is

OH, F, Cl, $OC(O)CH_3$ or H, preferably OH, F or H, in particular F or H is preferred here.

In a preferred embodiment, in compounds according to formula I, 3 or 4 of the radicals $R^9$ to $R^{13}$ correspond to H, and the others independently of one another are H, Cl, F, OH, $CF_2H$, $CF_3$ or $C_{1-4}$-alkyl, saturated and unsubstituted, branched or unbranched; or $OR^{14}$ or $SR^{14}$, where $R^{14}$ is $C_{1-3}$-alkyl, saturated and unsubstituted, branched or unbranched;

preferably H, Cl, F, OH, $CF_2H$, $CF_3$, $OCH_3$ or $SCH_3$ or $R^{12}$ and $R^{11}$ form a 3,4-$OCH=CH$ ring, in particular, if $R^9$, $R^{11}$ and $R^{13}$ correspond to H, one of $R^{10}$ or $R^{12}$ also corresponds to H, while the other is Cl, F, OH, $CF_2H$, $CF_3$, OR or $SR^{14}$, preferably OH, $CF_2H$, $OR^{14}$ or $SCH_3$, in particular OH or $OC_{1-3}$-alkyl, preferably OH or $OCH_3$, or if $R^9$ and $R^{13}$ correspond to H and $R^{11}$ corresponds to OH, $OCH_3$, Cl or F, preferably Cl, one of $R^{10}$ or $R^{12}$ also corresponds to H, while the other corresponds to OH, $OCH_3$, Cl or F, preferably Cl, or if $R^9$, $R^{10}$, $R^{12}$ and $R^{13}$ correspond to H, $R^{11}$ is $CF_3$, $CF_2H$, Cl or F, preferably F, or if $R^{10}$, $R^{11}$ and $R^{12}$ correspond to H, one of $R^9$ or $R^{13}$ also corresponds to H, while the other is OH, $OC_2H_5$ or $OC_3H_7$.

The use of compounds according to formula I wherein $R^9$, $R^{11}$ and $R^{13}$ correspond to H, one of $R^{10}$ or $R^{12}$ also corresponds to H, while the other is:

Cl, F, OH, SH, $CF_2H$, $CF_3$, $OR^{14}$ or $SR^{14}$, preferably OH or $OR^{14}$, in particular OH or $OC_{1-3}$-alkyl, preferably OH or $OCH_3$, is furthermore preferred.

It is also preferred if a compound according to formula I are present in the form of a diastereomer with the relative configuration Ia

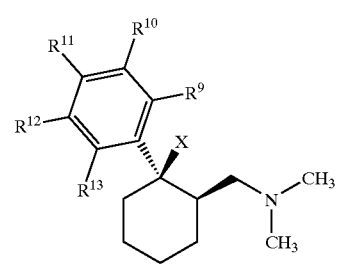

Ia in particular are used in mixtures with a higher content of this diastereomer compared with the other diastereomers or as a pure diastereomer.

It is furthermore preferred if the compounds of the formula I are used in the form of the (+)-enantiomer, in particular in mixtures with a higher content of the (+)-enantiomer compared with the (−)-enantiomer of a racemic compound or as the pure (+)-enantiomer.

In general, in the preferred use of the (+)-enantiomer also a smaller content of (−)-enantiomer with respect to the (+)-enantiomer is acceptable and may be—but does not have to be—contained in the use according to the invention.

The use of a compound chosen from the following group is particularly preferred:

(+)-(1R,2R)-3-(2-dimethylaminomethyl-1-fluoro-cyclohexyl)-phenol, (+)-(1S,2R)-3-(2-dimethylaminomethyl-cyclohexyl)-phenol or (−)-(1R,2S)-3-(2-dimethylaminomethyl-cyclohexyl)-phenol, preferably as the respective hydrochloride.

Although the uses according to the invention merely display mild side effects, it may be of advantage, for example to avoid certain forms of dependency, also to use morphine antagonists, in particular naloxone, naltrexone and/or levallorphan, in addition to compounds according to general formula I.

The invention also relates to medicaments for treatment of an increased urge to urinate or urinary incontinence which comprise as the active compound at least one 6-dimethylaminomethyl-1-phenyl-cyclohexane compound according to general formula I

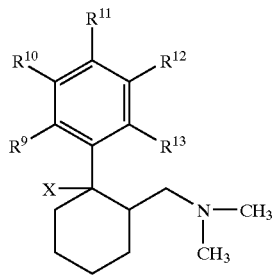

wherein

X is OH, F, Cl, H or OC(O)$R^7$, where $R^7$ is $C_{1-3}$-alkyl, branched or unbranched, saturated or unsaturated, unsubstituted or mono- or polysubstituted, and $R^9$ to $R^{13}$ in each case independently of one another are H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$, $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, CO—$C_6H_4$—$R^{15}$, where $R^{15}$ is ortho-OCO$C_{1-3}$-alkyl or meta- or para-$CH_2N(R^{16})_2$, where $R^{16}$ is $C_{1-4}$-alkyl or 4-morpholino, it being possible for the alkyl groups in the radicals $R^{14}$, $R^{15}$ and $R^{16}$ to be branched or unbranched, saturated or unsaturated, unsubstituted or mono- or polysubstituted;

where $R^{17}$ and $R^{18}$ in each case independently of one another are H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, OCH═CH, CH═CHO, CH═C(CH3)O, OC(CH3)═CH, $(CH_2)_4$ or OCH═CHO ring, in the form of their racemates; enantiomers, diastereomers, in particular mixtures of their enantiomers or diastereomers, or of an individual enantiomer or diastereomer; their bases and/or salts of physiologically acceptable acids and optionally one or more additives and/or auxiliary substances.

The present invention shows that the pharmaceutical compositions of the present invention comprising compounds of formula I have higher activities for treating urinary incontinence than tramadol. Tramadol is known and does not fall within this invention. In other words, medicaments comprising a compound according to formula I in which X corresponds to OH if $R^9$, $R^{11}$ and $R^{13}$ correspond to H and one of $R^{10}$ or $R^{12}$ corresponds to H and the other corresponds to $OCH_3$ are excluded.

Suitable salts in the context of this invention and in the medicaments claimed are salts of the particular active compound with inorganic or organic acids and/or a sugar substitute, such as saccharin, cyclamate or acesulfam. However, the hydrochloride is particularly preferred.

Suitable additives and/or auxiliary substances in the context of this invention are well-known to those ordinarily skilled in the art for pharmaceutical formulations. The choice of these auxiliary substances and the amounts thereof to be employed depend on whether the medicament is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration of the skin, are examples of suitable percutaneous administration forms. Examples of auxiliary substances and additives for oral administration forms are disintegrants, lubricants, binders, fillers, mould release agents, where appropriate solvents, flavouring substances, sugar, in particular carrier agents, diluents, dyestuffs, antioxidants etc. Waxes or fatty acid esters, inter alia, can be used for suppositories, and carrier substances, preservatives, suspension auxiliaries etc. can be used for compositions for parenteral administration.

The amounts of active compound to be administered to patients vary according to the weight of the patient, the mode of administration and the severity of the disease. The compounds according to the invention can be released in a delayed manner from formulation forms which can be used orally, rectally or percutaneously. Appropriate sustained release formulations, in particular in the form of a "once daily" preparation which has to be taken only once a day, are particularly preferred for the indication according to the invention.

Medicaments which comprise at least 0.05 to 90.0% of the active compound, in particular low active dosages, in order to avoid side effects or analgesic actions, are furthermore preferred. 0.1 to 5,000 mg/kg, in particular 1 to 500 mg/kg, preferably 2 to 250 mg/kg of body weight of at least one compound of the formula I are conventionally administered. However, administration of 0.01–5 mg/kg, preferably 0.03 to 2 mg/kg, in particular 0.05 to 1 mg/kg of body weight, is also preferred and conventional.

Auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The medicaments and pharmaceutical compositions according to the invention are prepared with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

For example, for a solid formulation, such as a tablet, the active compound of the medicament, i.e. a compound of the general structure I or one of its pharmaceutically acceptable salts, can be granulated with a pharmaceutical carrier, e.g. conventional tablet constituents, such as maize starch, lactose, sucrose, sorbitol, talc, magnesium stearate, dicalcium phosphate or pharmaceutically acceptable gums, and pharmaceutical diluents, such as water, in order to form a solid composition which comprises a compound according to the invention or a pharmaceutically acceptable salt thereof in homogeneous distribution. Homogeneous distribution is understood here as meaning that the active compound is distributed uniformly over the entire composition, so that this can easily be divided into unit dose forms, such as tablets, pills or capsules, having the same action. The solid composition is then divided into unit dose forms. The tablets or pills of the medicament according to the invention or of the compositions according to the invention can also be coated or compounded in another manner in order to provide a dose form with delayed release. Suitable coating agents are, inter alia, polymeric acids and mixtures of polymeric acids with materials such as e.g. shellac, cetyl alcohol and/or cellulose acetate.

Although the medicaments according to the invention merely display mild side effects, it may be of advantage, for example to avoid certain forms of dependency, also to use morphine antagonists, in particular naloxone, naltrexone and/or levallorphan, in addition to the compounds according to general formula I.

Medicaments are preferred in which compounds according to general formula I wherein X is OH, F, Cl, OC(O)CH$_3$ or H, preferably OH, F or H, in particular F or H are used.

It is furthermore preferred if compounds according to general formula I wherein 3 or 4 of the radicals $R^9$ to $R^{13}$ must correspond to H, and the others independently of one another are H, Cl, F, OH, CF$_2$H, CF$_3$ or C$_{1-4}$-alkyl, saturated and unsubstituted, branched or unbranched; OR$^{14}$ or SR$^{14}$, where $R^{14}$ is C$_{1-3}$-alkyl, saturated and unsubstituted, branched or unbranched;
preferably H, Cl, F, OH, CF$_2$H, CF$_3$, OCH$_3$ or SCH$_3$ or $R^{12}$ and $R^{11}$ form a 3,4-OCH=CH ring in particular compounds wherein if $R^9$, $R^{11}$ and $R^{13}$ correspond to H, one of $R^{10}$ or $R^{12}$ also corresponds to H, while the other is:

Cl, F, OH, CF$_2$H, CF$_3$, OR$^{14}$ or SR$^{14}$, preferably OH, CF$_2$H, OR$^{14}$ or SCH$_3$, in particular OH or OC$_{1-3}$-alkyl, preferably OH or OCH$_3$, or if $R^9$ and $R^{13}$ correspond to H and $R^{11}$ corresponds to OH, OCH$_3$, Cl or F, preferably Cl, one of $R^{10}$ or $R^{12}$ also corresponds to H, while the other corresponds to OH, OCH$_3$, Cl or F, preferably Cl, or if $R^9$, $R^{10}$, $R^{12}$ and $R^{13}$ correspond to H, $R^{11}$ is CF$_3$, CF$_2$H, Cl or F, preferably F, or if $R^{10}$, $R^{11}$ and $R^{12}$ correspond to H, one of $R^9$ or $R^{13}$ also corresponds to H, while the other is OH, OC$_2$H$_5$ or OC$_3$H$_7$, are used in the medicaments according to the invention.

Medicaments in which compounds according to general formula I wherein $R^9$, $R^{11}$ and $R^{13}$ correspond to H, one of $R^{10}$ or $R^{12}$ also corresponds to H, while the other is:

Cl, F, OH, SH, CF$_2$H, CF$_3$, OR$^{14}$ or SR$^{14}$, preferably OH or OR$^{14}$, in particular OH or OC$_{1-3}$-alkyl, preferably OH or OCH$_3$, are used are also preferred.

It is furthermore preferred if compounds according to general formula I which are present in the form of the diastereomer with the relative configuration Ia

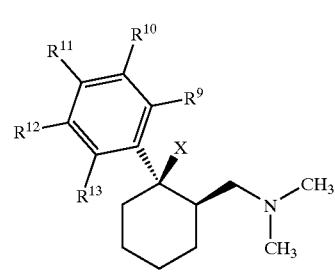

Ia in particular in mixtures with a higher content of this diastereomer compared with the other diastereomer or as the pure diastereomer, are contained in the medicaments according to the invention.

It is furthermore preferred if compounds according to general formula I which are present in the form of the (+)-enantiomer, in particular in mixtures with a higher content of the (+)-enantiomer compared with the (−)-enantiomer of a racemic compound or as the pure (+)-enantiomer, are contained in the medicaments according to the invention.

In general, in the preferred use of the (+)-enantiomer also a smaller content of (−)-enantiomer with respect to the (+)-enantiomer is acceptable and may be—but does not have to be—contained in the medicaments according to the invention.

Medicaments according to the invention which comprise at least one compound chosen from the following group:

(+)-(1R,2R)-3-(2-dimethylaminomethyl-1-fluoro-cyclohexyl)-phenol, (+)-(1S,2S)-3-(2-dimethylaminomethyl-cyclohexyl)-phenol and (−)-(1R,2R)-3-(2-dimethylaminomethyl-cyclohexyl)-phenol, preferably as the hydrochloride, are particularly preferred.

The invention also relates to a method for treatment of an increased urge to urinate or urinary incontinence in which the 6-dimethylaminomethyl-1-phenyl-cyclohexane compounds according to general formula I in the form of a racemate; an enantiomer, a diastereomer, in particular a mixture of enantiomers or diastereomers; as the free base and/or in the form of physiologically acceptable salts are used.

The following examples are intended to illustrate the invention without the subject matter of the invention being limited thereto.

EXAMPLES

Example 1

List of Substances Tested

Table I lists the compounds tested for their activity.

TABLE 1

Substances Tested

| Name | Cmpd. no. |
|---|---|
| (+)-(1R,2R)-3-(2-Dimethylaminomethyl-1-fluoro-cyclohexyl)-phenol, hydrochloride | 18G26 |
| (+)-(1S,2S)-3-(2-Dimethylaminomethyl-cyclohexyl)-phenol, hydrochloride | 19 |
| (−)-(1R,2R)-3-(2-Dimethylaminomethyl-cyclohexyl)-phenol, hydrochloride | 20 |
| rac-Tramadol | 23 |

Example 2

Test System of Cystometry on Anaesthetized Naïve Rats

The cystometric investigation of naive female rats was carried out by the method of Kimura et al. (Kimura et al., 1996, Int. J. Urol. 3:218–227). The abdomen of anaesthetized ventilated rats is opened up and the ureter is tied off. The urine is drained from the kidneys. A catheter is inserted into the bladder and fixed. Saline is infused into the bladder via this by means of an infusion pump, until the bladder shows rhythmic spontaneous activity in the form of contractions, which can be recorded via a connected pressure transducer. After stable starting values are reached, the test substance is administered i.v. in a cumulative manner. An influence on bladder function manifests itself via suppression of spontaneous contractions. The absence of contractions over a period of 10 min is the parameter for the suppression.

A suppression of spontaneous contractions in rats was measurable with all the substances tested. Table II shows the mean of the lowest dose of 3 experiments at which for the first time contractions are absent over a period of 10 min.

TABLE II

Mean of Lowest Doses

| Cmpd. no. | Lowest dose (mg/kg) |
|---|---|
| 18 | 0.2 (n = 3) |
| 19 | 0.1 (n = 3) |
| 20 | 0.5 (n = 3) |
| 23 (Tramadol) | 5.3 (n = 3) |

TABLE II-continued

Mean of Lowest Doses

| Cmpd. no. | Lowest dose (mg/kg) |
|---|---|

Note: (n corresponds to the number of experiments used for calculating the mean)

The substances investigated show a positive action on bladder regulation and are thus suitable for treatment of urinary incontinence. They also appear superior to tramadol in this regard.

Example 3

Parenteral Administration Form 1 g of compound 19 is dissolved in 1 l of water for injection at room temperature and the solution is then adjusted to isotonic conditions by addition of NaCl.

What is claimed is:

1. A pharmaceutical composition for the treatment of an increased urge to urinate or urinary incontinence, comprising a pharmaceutically acceptable excipient and a compound of formula I:

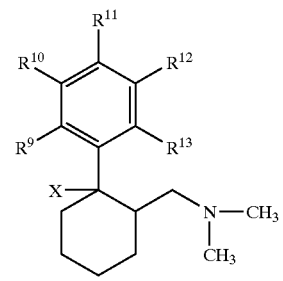

wherein
X is OH, F, Cl, H or OC(O)$R^7$, where $R^7$ is branched or unbranched, saturated or unsaturated, unsubstituted or mono- or polysubstituted $C_{1-3}$-alkyl, and
$R^9$, $R^{10}$ and $R^{13}$ each independently of one another is H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$, $SO_2CH_3$, $SO_2CF_3$, CN, $COOR^{14}$, $NO_2$, $CONR^{17}R^{18}$; branched or unbranched, saturated or unsaturated, unsubstituted or mono- or polysubstituted $C_{1-6}$-alkyl; or unsubstituted or mono- or polysubstituted phenyl;
where $R^{14}$ is $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, or CO—$C_6H_4$—$R^{15}$,
where $R^{15}$ is ortho-OCO$C_{1-3}$-alkyl or meta- or para-$CH_2N(R^{16})_2$, where $R^{16}$ is $C_{1-4}$-alkyl or 4-morpholino, and $R^{17}$ and $R^{18}$ each independently of one another is H; $C_{1-6}$-alkyl; phenyl, benzyl, or phenethyl, in each case unsubstituted or mono- or polysubstituted, wherein for $R^{14}$, $R^{15}$, $R^{16}$ $R^{17}$ and $R_{18}$, the alkyl groups maybe branched or unbranched, saturated or unsaturated, unsubstituted or mono- or polysubstituted; and $R^{12}$ and $R^{11}$ form a 3,4-OCH=CH ring;

wherein the compound of formula I is in the form of a racemate, an enantiomer, a diastereomer, a mixture of enantiomers, a mixture of diastereomers, a free base, or a salt of a physiologically acceptable acid.

2. A pharmaceutical composition for the treatment of an increased urge to urinate or urinary incontinence, comprising a pharmaceutically acceptable excipient and a compound of formula I:

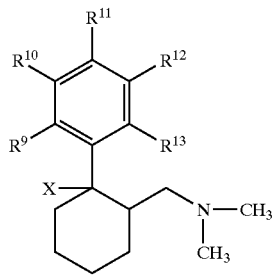

wherein

X is OH, F, Cl, H or OC(O)$R^7$, where $R^7$ is branched or unbranched, saturated or unsaturated, unsubstituted or mono- or polysubstituted $C_{1-3}$-alkyl;

$R^9$ and $R^{13}$ are H, $R^{11}$ is OH, OCH$_3$, Cl or F, and one of $R^{10}$ and $R^{12}$ is also H, while the other is OH, OCH$_3$, Cl or F;

wherein the compound of formula I is in the form of a racemate, an enantiomer, a diastereomer, a mixture of enantiomers, a mixture of diastereomers, a free base, or a salt of a physiologically acceptable acid.

3. A pharmaceutical composition according to claim 2, wherein $R^{11}$ is Cl.

4. A pharmaceutical composition according to claim 2, wherein one of $R^{10}$ and $R^{12}$ is H, while the other Cl.

5. A pharmaceutical composition for the treatment of an increased urge to urinate or urinary incontinence, comprising a pharmaceutically acceptable excipient and a compound of formula I:

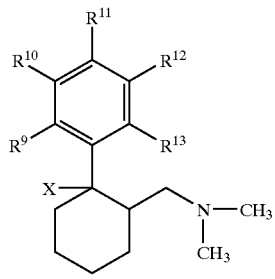

wherein

X is OH, F, Cl, H or OC(O)$R^7$, where $R^7$ is branched or unbranched, saturated or unsaturated, unsubstituted or mono- or polysubstituted $C_{1-3}$-alkyl;

$R^9$, $R^{10}$, $R^{12}$ and $R^{13}$ are H, and $R^{11}$ is CF$_3$, CF$_2$H, Cl or F;

wherein the compound of formula I is in the form of a racemate, an enantiomer, a diastereomer, a mixture of enantiomers, a mixture of diastereomers, a free base, or a salt of a physiologically acceptable acid.

6. A pharmaceutical composition according to claim 5, wherein $R^{11}$ is F.

7. A pharmaceutical composition for the treatment of an increased urge to urinate or urinary incontinence, comprising a pharmaceutically acceptable excipient and a compound of formula I:

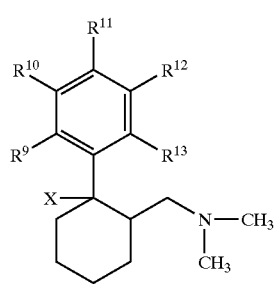

wherein

X is OH, F, Cl, H or OC(O)$R^7$, where $R^7$ is branched or unbranched, saturated or unsaturated, unsubstituted or mono- or polysubstituted $C_{1-3}$-alkyl;

$R^{10}$, $R^{11}$ and $R^{12}$ are H, and one of $R^9$ and $R^{13}$ is also H, while the other is OH, OC$_2$H$_5$ or OC$_3$H$_7$;

wherein the compound of formula I is in the form of a racemate, an enantiomer, a diastereomer, a mixture of enantiomers, a mixture of diastereomers, a free base, or a salt of a physiologically acceptable acid.

8. A pharmaceutical composition according to claim 1, 2, 5 or 7, wherein the compound of formula I is present in the form of a diastereomer having a configuration of formula Ia:

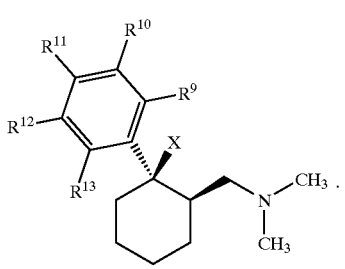

9. A pharmaceutical composition according to claim 8, wherein other diastereomers of the compound are not present or are present in a proportion lower than the diastereomer of formula Ia.

10. A pharmaceutical composition according to claim 1, 2, 5 or 7, wherein the (+)-enantiomer of the compound is not present or is present in a proportion lower than the (−)-enantiomer.

11. A pharmaceutical composition according to claim 1, 2, 5 or 7, wherein the compound is in the form of a hydrochloride.

12. A method for treating increased urge to urinate or urinary incontinence, comprising administering to a patient in need thereof an effective amount of a pharmaceutical composition comprising a pharmaceutically acceptable excipient and a compound formula I:

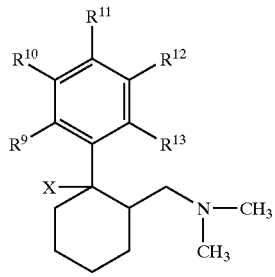

wherein

X is OH, F, Cl, H or OC(O)R$^7$, where R$^7$ is branched or unbranched, saturated or unsaturated, unsubstituted or mono- or polysubstituted C$_{1-3}$-alkyl, and R$^9$ to R$^{13}$ each independently of one another is H, F, Cl, Br, I, CH$_2$F, CHF$_2$, CF$_3$, OH, SH, OR$^{14}$, OCF$_3$, SR$^{14}$, NR$^{17}$R$^{18}$, SOCH$_3$, SOCF$_3$; SO$_2$CH$_3$, SO$_2$CF$_3$, CN, COOR$^{14}$, NO$_2$, CONR$^{17}$R$^{18}$; branched or unbranched, saturated or unsaturated, unsubstituted or mono- or polysubstituted C$_{1-6}$-alkyl; or unsubstituted or mono- or polysubstituted phenyl;

where R$^{14}$ is C$_{1-6}$alkyl; pyridyl, thienyl, thiazolyl, phenyl, benzyl or phenethyl, in each case unsubstituted or mono- or polysubstituted; PO(O—C$_{1-4}$-alkyl)$_2$, CO(OC$_{1-5}$-alkyl), CONH—C$_6$H$_4$—(C$_{1-3}$-alkyl), CO(C$_{1-5}$-alkyl), CO—CHR$^{17}$—NHR$^{18}$, or CO—C$_6$H$_4$—R$^{15}$, where R$^{15}$ is ortho-OCOC$_{1-3}$-alkyl or meta- or para-CH$_2$N(R$^{16}$)$_2$, where R$^{16}$ is C$_{1-4}$-alkyl or 4-morpholino, and R$^{17}$ and R$^{18}$ each independently of one another is H; C$_{1-6}$-alkyl; phenyl, benzyl or phenethyl, in each case unsubstituted or mono- or polysubstituted, wherein for R$^{14}$, R$^{15}$, R$^{16}$ R$^{17}$ and R$^{18}$, the alkyl groups maybe branched or unbranched, saturated or unsaturated, unsubstituted or mono- or polysubstituted; or R$^9$ and R$^{10}$, or R$^{10}$ and R$^{11}$, or R$^{12}$ and R$^{11}$ together form an OCH$_2$O, OCH$_2$CH$_2$O, OCH=CH, CH=CHO, CH=C(CH3)O, OC(CH3)=CH, (CH$_2$)$_4$ or OCH=CHO ring, with the proviso that if R$^9$, R$^{11}$ and R$^{13}$ are H, and one of R$^{10}$ or R$^{12}$ is H and the other is OCH$_3$, X is not OH, wherein the compound of formula I is in the form of a racemate, an enantiomer, a diastereomer, a mixture of enantiomers, a mixture of diastereomers, a free base, or a salt of a physiologically acceptable acid.

13. A method according to claim 12, wherein X is OH, F, Cl, OC(O)CH$_3$ or H.

14. A method according to claim 13, wherein X is OH, F or H.

15. A method according to claim 14, wherein X is F or H.

16. A method according to claim 12, wherein at least three of R$^9$ to R$^{13}$ are H, and the others are independently of one another H, Cl, F, OH, CF$_2$H, CF$_3$; C$_{1-4}$-alkyl, saturated and unsubstituted, branched or unbranched; OR$^{14}$ or SR$^{14}$, where R$^{14}$ is saturated and unsubstituted, branched or unbranched C$_{1-3}$-alkyl.

17. A method according to claim 16, wherein at least three of R$^9$ to R$^{13}$ are H, and the others are independently of one another H, Cl, F, OH, CF$_2$H, CF$_3$, OCH$_3$ or SCH$_3$.

18. A method according to claim 12, wherein R$^2$ and R$^{11}$ form a 3,4-OCH=CH ring.

19. A method according to claim 16, wherein R$^9$ and R$^{13}$ are H; R$^{11}$ is OH, OCH$_3$, Cl or F; and one of R$^{10}$ and R$^{12}$ is also H, while the other is OH, OCH$_3$, Cl or F.

20. A method according to claim 19, wherein R$^{11}$ is Cl.

21. A method according to claim 19, wherein one of R$^{10}$ and R$^{12}$ is H, while the other is Cl.

22. A method according to claim 16, wherein at least four of R$^9$ to R$^{13}$ are H.

23. A method according to claim 22, wherein at least four of R$^9$ to R$^{13}$ are H, and the others are independently of one another H, Cl, F, OH, CF$_2$H, CF$_3$, OCH$_3$ or SCH$_3$.

24. A method according to claim 22, wherein R$^9$, R$^{11}$ and R$^{13}$ are H; and one of R$^{10}$ or R$^{12}$ is also H, while the other is Cl, F, OH, CF$_2$H, CF$_3$, OR$^{14}$ or SR$^{14}$.

25. A method according to claim 24, wherein R$^9$, R$^{11}$ and R$^{13}$ are H; and one of R$^{10}$ or R$^{12}$ is also H, while the other is OH, CF$_2$H, OR$^{14}$ or SCH$_3$.

26. A method according to claim 25, wherein R$^9$, R$^{11}$ and R$^{13}$ are H; and one of R$^{10}$ or R$^{12}$ is also H, while the other is OH or OC$_{1-3}$-alkyl.

27. A method according to claim 23, wherein R$^9$, R$^{11}$ and R$^{13}$ are H; and one of R$^{10}$ or R$^{12}$ is also H, while the other is OH or OCH$_3$.

28. A method according to claim 22, wherein R$^9$, R$^{10}$, R$^{12}$ and R$^{13}$ are H, and R$^{11}$ is CF$_3$, CF$_2$H, Cl or F.

29. A method according to claim 28, wherein R$^{11}$ is F.

30. A method according to claim 22, wherein R$^{10}$, R$^{11}$ and R$^{12}$ are H; and one of R$^9$ and R$^{13}$ is also H, while the other is OH, OC$_2$H$_5$ or OC$_3$H$_7$.

31. A method according to claim 22, wherein the compound of formula I is present in the form of a diastereomer having a configuration of formula Ia:

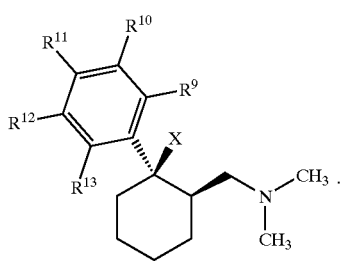

32. A method according to claim 31, wherein other diastereomers of the compound are not present or are present in a proportion lower than the diastereomer of formula Ia.

33. A method according to claim 12, wherein the (+)-enantiomer of the compound is not present or is present in a proportion lower than the (−)-enantiomer.

34. A method according to claim 12, wherein the compound is selected from the group consisting of:

(+)-(1R,2R)-3-(2-dimethylaminomethyl-1-fluoro-cyclohexyl)-phenol, (+)-(1S,2S)-3-(2-dimethylaminomethyl-cyclohexyl)-phenol, and (−)-(1R,2R)-3-(2-dimethylaminomethyl-cyclohexyl)-phenol.

35. A method according to claim 34, wherein the compound is in the form of a hydrochloride.

* * * * *